United States Patent [19]

Crossley

[11] Patent Number: 4,609,655
[45] Date of Patent: Sep. 2, 1986

[54] ANTI-ULCER IMIDAZO-QUINOLINE, INDOLE AND BENZAZEPINE DERIVATIVES

[75] Inventor: Roger Crossley, Berkshire, England

[73] Assignee: John Wyeth & Brother, Ltd., Maidenhead, England

[21] Appl. No.: 772,990

[22] Filed: Sep. 6, 1985

Related U.S. Application Data

[63] Continuation-in-part of Ser. No. 677,789, Dec. 4, 1984, abandoned.

[30] Foreign Application Priority Data

Dec. 16, 1983 [GB] United Kingdom ............... 8333581

[51] Int. Cl.$^4$ ............... C07D 471/06; C07D 487/06; A61K 31/415
[52] U.S. Cl. ............... 514/214; 514/292; 514/395; 546/86; 548/324; 540/579
[58] Field of Search ............... 546/86; 548/324; 260/245.6; 514/214, 292, 395

[56] References Cited

U.S. PATENT DOCUMENTS 4,478,834  10/1984  Shroff et al. ............... 546/81

FOREIGN PATENT DOCUMENTS 2039218B  7/1983  United Kingdom .

OTHER PUBLICATIONS

Chemical Abstracts 79: 126396h.
Il'ina, I. G. et al, Khim. Geterotsikl. Soedin. 1973, (8), pp. 1112–1114.
Meth-Cohn, O. et al, J. Chem. Soc. 1964 pp. 2609–2614.
Current Abstracts of Chemistry, 51 (519) 210074 (1973).
Richardson, A., J. Org. Chem. 28 p. 2581 (1963).
Richardson, A., J. Org. Chem. 25 p. 1138 (1980).
Saari, W. S. et al. J. Heterocyclic Chem. 19 p. 837 (1982).

*Primary Examiner*—Henry R. Jiles
*Assistant Examiner*—Dale A. Bjorkman
*Attorney, Agent, or Firm*—George Tarnowski

[57] ABSTRACT

The invention provides a compound of formula I

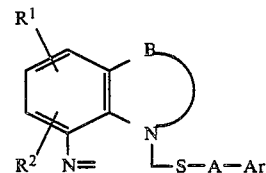

wherein
A is a $C_1$–$C_4$ straight or branched alkylene chain which may be saturated or unsaturated,
B is a $C_2$–$C_4$ straight or branched alkylene chain which may be saturated or unsaturated,
Ar is a phenyl or naphthyl group which may be substituted or unsubstituted,
$R^1$ and $R^2$ are the same or different and are hydrogen, alkyl, alkoxy, alkoxyalkyl, hydroxyalkyl, hydroxy, halogen, nitro, carboxy, a carboxylic alkyl ester, carbamoyl, carbamoyloxy, cyano, acyl, acylamino or trifluoromethyl, or an acid addition salt thereof.

The compounds are useful for the treatment of ulcers or hypersecretion in mammals. Pharmaceutical compositions containing the novel compounds and processes for their preparation are described.

9 Claims, No Drawings

4,609,655

ANTI-ULCER IMIDAZO-QUINOLINE, INDOLE AND BENZAZEPINE DERIVATIVES

This application is a continuation-in-part of Ser. No. 677,789 filed 12-4-84, abandoned.

The invention relates to novel heterocyclic compounds useful for the treatment of ulcers or hypersecretion in mammals and pharmaceutical compositions containing the novel compounds.

In our GB Pat. No. 2039218 B we have described inter alia phenylalkylthiopyridines which are useful in the treatment of ulcers or hypersecretion in mammals. We have now found that by modifying the molecule to replace the pyridine group by an imidazoquinoline group novel compounds are obtained which have one or more of the following activities, anti-ulcer, anti-secretory or $H^+/K^+$ATPase inhibitory activity.

The invention provides a compound of formula I $$\text{(I)}$$

wherein

A is a $C_1$-$C_4$ straight or branched alkylene chain which may be saturated or unsaturated, B is a $C_2$-$C_4$ straight or branched alkylene chain which may be saturated or unsaturated, Ar is a phenyl or naphthyl group which may be substituted or unsubstituted, $R^1$ and $R^2$ are the same or different and are hydrogen, alkyl, alkoxy, alkoxyalkyl, hydroxyalkyl, hydroxy, halogen nitro, carboxy, a carboxylic alkyl ester, carbamoyl, carbamoyloxy, cyano, acyl, acylamino e.g. loweralkanoylamino such as acetamino or trifluoromethyl, and acid addition salts thereof.

Examples of A are $CH_2$, $CH(CH_3)$, $CH(CH_3)CH_2$, $CH_2CH_2$, $CH_2CH_2CH_2$, $CH=CH$, and $CH=CHCH_2$. $CH_2$ is preferred.

B may be for example $CH_2CH_2$, $CH(CH_3)CH_2$, $CH_2CH_2CH_2$, $CH=CH$, $CH=CHCH_2$ or $(CH_2)_4$ The group Ar may be mono or polysubstituted but is preferably mono or disubstituted by any of the following; halogen, alkoxy, aralkoxy, hydroxy, hydroxyalkyl, alkoxyalkyl, trifluoromethyl, alkyl, aryl or aralkyl e.g. of 7 to 12 carbon atoms or disubstituted by a loweralkylene-dioxy radical of 1 to 6 carbon atoms.

In this specification an alkyl group is preferably lower alkyl i.e. of 1 to 6 carbon atoms e.g. methyl, ethyl, n-propyl, isopropyl, n-butyl, s-butyl, t-butyl, n-pentyl or n-hexyl. An alkoxy group is preferably lower alkoxy in which the alkyl portion is as defined for a lower alkyl group. A carboxylic alkyl ester group is preferably lower alkoxy carbonyl. Whenever the term lower alkyl or lower alkoxy is used as part of another group e.g. arylloweralkyl, the lower alkyl or lower alkoxy portion has 1 to 6 carbon atoms unless otherwise stated. An aralkyl radical is preferably aryllower alkyl e.g. benzyl, phenethyl or phenpropyl.

The acid addition salts of compounds of formula I may be of any pharmaceutically acceptable organic or inorganic acid e.g. hydrochloric, hydrobromic, hydroiodic, phosphoric, sulphuric, nitric, citric, acetic, formic, fumaric, maleic, tartaric, embonic, malonic, alkylsulphonic, e.g. methanesulphonic, arylsulphonic e.g. p-toluene sulphonic acids.

The invention includes methods of preparing the compounds of formula I. The preferred method comprises reacting a compound of formula II, $$\text{Ar—A—Hal} \qquad \text{(II)}$$

wherein Ar and A are as defined above and Hal is a halogen atom especially chlorine, bromine or iodine, with a thiol of formula III, or an alkali metal salt thereof, $$\text{(III)} \qquad \text{(IIIa)}$$

wherein B, $R^1$ and $R^2$ are as defined above.

Alternatively a compound of formula Ar—A—SH (IIa), an alkali metal salt thereof may be reacted with a halide of formula IIIa wherein $R^1$, $R^2$, B and Hal are as defined above.

The starting compounds of formula II and IIa are known compounds or may be prepared by methods known for analogous compounds. The starting compounds of formula III or IIIa are known compounds described in for example J. Org. Chem. 1960, 25, 1138 or 1963, 28, 2581, J. Heterocyclic Chem. 1982, 19, 837 or may be prepared by methods known for analogous compounds. In the above mentioned reaction the compounds of formula I may be isolated in free base form or as acid addition salts.

The compounds of formula I possess anti-ulcer and/or anti-secretory activity as measured by standard test procedures and accordingly are useful for the treatment of ulcers or hypersecretion in mammals.

Anti-ulcer activity was determined by the stressinduced erosion test of Senay and Levine, Proc. Soc. Exp. Biol. Med., 124, 1221-3 (1967).

Anti-secretory activity was determined by the test of H. Shay, D. Sun and H. Gruenstein, Gastroenterology, 1954, 26, 903-13 as exemplified by Beattie et al, J. Med. Chem. 20, 714 (1977).

Compounds of formula I were also tested for anti-secretory activity by their ability to inhibit the highly specific proton transporting enzyme $H^+/K^+$ATPase.

Potential $H^+/K^+$ATPase inhibitors are evaluated by a technique involving the measurement of aminopyrine accumulation in rabbit isolated gastric glands. Amino-pyrine, which is a weak base, accumulates in acid-secreting cells; therefore, uptake of aminopyrine is increased by secretagogues and an inhibitor of acid secretion will reduce the response to one or more secretagogues depending upon its site of action. Compounds which reduce the response to dibutyryl cyclic adenosine monophosphate (DBcAMP) stimulation are assumed to have an intracellular site of action, and those which reduce the response to both DBcAMP and high potassium ion concentration (K+) are thought to have an intracellular site of action at the secretory surface of the parietal cell, involving the highly specific proton—transporting enzyme, H+/K+ATPase. The following test procedure is used:

Rabbit gastric glands are isolated from gastric mucosa from the corpus region of the stomach by a method based on one described by Berglindh T., Obrink K. J., Acta Physiol. Scand. 96, 150-159 (1976). Measurement of aminopyrine uptake is carried out using a modification of the method described by Berglindh T., Hellander H. F., Obrink K. J. (ibid, 97, 401-414, 1976).

Compounds are tested at a concentration of $10^{-4}$M, initially, and in some cases at lower concentrations, for their ability to inhibit $^{14}$C-aminopyrine uptake in gastric glands, stimulated by DBcAMP and high K+ respectively. Results are expressed as the % inhibition of the maximum response to the secretagogue induced by the test compound. An inhibitor of H+/K+ATPase would be expected to reduce the response to both secretagogues.

The pharmaceutical formulations include solids and liquids. Any suitable carrier known in the art can be used to prepare the pharmaceutical composition. In such a composition, the carrier is generally a solid or liquid, or a mixture of a solid and a liquid.

Solid form compositions include powders, granules, tablets, capsules (e.g. hard and soft gelatin capsules). A solid carrier can be, for example, one or more substances which may also act as flavouring agents, lubricants, solubilisers, suspending agents, fillers, glidants, compression aids, binders, effervescent excipients or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 10 to 80%, preferably 25 to 75% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidone, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, suspensions, emulsions, syrups and elixirs. The active ingredient, for example, can be suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavouring agents, suspending agents, thickening agents, colours, viscosity regulators, stabilisers or osmo-regulators. Suitable examples of liquid carriers for oral administration include water (particularly containing additives as above e.g. cellulose derivatives, preferably sodium carboxymethyl cellulose solution) alcohols (including monohydric alcohols and polyhydric alcohols e.g. glycerol and glycols) and their derivatives, and oils (e.g. fractionated coconut oil and arachis oil).

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders. The unit dosage form can be, for example, a capsule or tablet itself, or it can be the appropriate number of any such compositions in package form. The quantity of the active ingredient in a unit dose of composition may be varied or adjusted from 10 mg or less to 500 mg or more, according to the particular need.

The anti-ulcer compositions of the invention will be administered orally on either liquid or solid composition form. These compositions may include one or more antacid ingredients, e.g. aluminium hydroxide, magnesium hydroxide or bismuth carbonate, aluminium glycinate, calcium carbonate, magnesium trisilicate, sodium bicarbonate or the alumina gel described in British Specification No. 1,284,394.

In another aspect the invention provides as pharmaceutical, e.g. an anti-ulcer agent a compound of formula I or a pharmaceutically acceptable salt thereof as defined above.

The compounds of the invention may be used in treating ulcers or hypersecretion in a mammal in need of such treatment by administering to said mammal an effective amount of a compound of formula I or a pharmaceutically acceptable salt thereof. The amount of compound used will depend on the activity of the compound and the needs of the mammal being treated. Doses may range from 0.1 to 30 mg/kg.

The following examples illustrate the invention:

EXAMPLE 1

2-Benzylthio-5,6,-dihydro-[4H]-imidazo[4,5,1-ij]-quinoline

A solution of 5,6-dihydro-2-mercapto-[4H]-imidazo-[4,5,1-ij]quinoline (3.5g) in ethanol (50ml) at reflux was treated with benzyl chloride (3.5ml) and heated at reflux for 3 hours. The solution was cooled and induced to crystallise. The crystals which formed were filtered, washed with ether and dried to give the title compound as the hydrochloride (5.6g) mp 168°-9° C. (Found: C,64.2; H,5.4; N,8.7 $C_{11}H_{10}N_2S \cdot HCl$ requires C,64.4; H,5.4; N,8.3%.

EXAMPLE 2

2-(3-Chlorobenzylthio)-5,6,-dihydro-[4H]-imidazo[4,5,1,-ij]quinoline

A solution of 5,6-dihydro-2-mercapto-[4H]-imidazo-[4,5,1-ij]quinoline (3.5g) in ethanol (50ml) at reflux was treated with m-chlorobenzyl chloride (3.5ml) and was heated at reflux for 3 hours. Crystals which formed on cooling were removed by filtration, washed with $Et_2O$ and dried to give the title compound as the hydrochloride (5.3g) mp 172°-5° C. (Found: C,58.1; H,4.6; N,8.0 $C_{17}H_{15}ClN_2S.HCl$ requires C,57.8; H,4.65; H,8.1%).

EXAMPLE 3

5,6-Dihydro-2-(4-fluorophenylmethylthio)-[4H]-imidazo-[4,5,1,-ij]quinoline

A suspension of 5,6-dihydro-2-mercapto-[4H]-imidazo-[4,5,1-i,j]quinoline in refluxing ethanol (25 ml) was treated with 4-fluorobenzyl chloride (1.45 g) in ethanol (5 ml). The solid rapidly went into solution and the mixture was heated at reflux for 1 hour and cooled. $Et_2O$ (150 ml) was added and the product allowed to crystallise. The crystals were removed by filtration, washed with $Et_2O$ and dried to give the title compound as the hydrochloride, hemihydrate (2.5 g, 73%) mp 118°-20° C. (Found: C,59.5; H,5.2; N,8.3 $C_{17}H_{15}FN_2S.HCl.\frac{1}{2}H_2O$ requires C,59.4; H,5.0; N,8.15%).

EXAMPLE 4

2-(2-Chlorophenylmethylthio)-5,6-dihydro-[4H]-imidazo-[4,5,1-ij]quinoline

A suspension of 5,6-dihydro-2-methyl-[4H]-imidazo-[4,5,1-i,j]quinoline (1.9 g) in refluxing ethanol (25 ml) was treated with o-chlorobenzyl chloride (1.61 g) in ethanol. The suspension rapidly went into solution and the mixture was heated at reflux for 2 hours, filtered, cooled and diluted with ether (150 ml). The crystals which formed were removed by filtration, washed with ether and dried to give the title compound as the hydrochloride (2.6 g, 74%) mp 157°-9° C. (Found: C,58.4; H,4.7; N,8.0 $C_{17}H_{15}ClN_2S.HCl$ requires C,58.1; H,4.6; N,8.0%).

EXAMPLE 5

2-(4-Chlorophenylmethylthio)-5,6-dihydro-[4H]-imidazo-[4,5,1-ij]quinoline

A suspension of 5,6-dihydro-2-mercapto-[4H]-imidazo-[4,5,1-i,j]quinoline (1.9 g) in refluxing ethanol (25 ml) was treated with 4-chlorobenzyl chloride (1.6 g) in ethanol (5 ml). The suspended solid rapidly went into solution and this was heated at reflux for 1 hour, filtered, cooled and diluted with ether (75 ml). The crystals which formed were removed by filtration, washed with ether and dried to give the title compound as the hydrochloride hemihydrate (1.8 g, 50%) mp 107°-8° C. (Found: C,56.8; H,5.0; N,7.7. $C_{17}H_{15}ClN_2S\ HCl\ \frac{1}{2}H_2O$ requires C,56.7; H,4.8; N,7.8%).

EXAMPLE 6

5,6-Dihydro-2-(2-fluorophenylmethylthio)-[4H]-imidazo-[4,5,1-ij]quinoline

A suspension of 5,6-dihydro-2-mercapto-[4H]-imidazo-[4,5,1-i,j]quinoline (1.9 g) in refluxing ethanol (25 ml) was treated with 2-fluorobenzyl chloride (1.45g) in ethanol (5 ml) and the mixture was heated at reflux for 1 hour. The resulting solution was filtered and ether (75 ml) was added. The crystals which formed on cooling were removed by filtration, washed with ether and dried to give the title compound as the hydrochloride (2.2 g, 65%) mp 167°-9° C. (Found: C,60.9; H,4.9; N,8.35. $C_{17}H_{15}FN_2S.HCl$ requires C,61.0; H,4.5; N,8.4%).

EXAMPLE 7

2-Benzylthio-[4H]-imidazo[4,5,1-ij]quinoline

2-Mercapto-[4H]-imidazo[4,5,1-ij]quinoline (1.88 g) in ethanol (20 ml) at reflux was treated with benzylchloride (1.2 ml) and the mixture was heated at reflux for $3\frac{1}{4}$ hours and cooled. The resulting mixture was diluted with ether (20 ml) and the cream coloured solid washed with ether and dried to give the title compound as the hydrochloride (2.7 g, 86%) mp 195°-8° C. (Found: C,64.6; H,4.9; N,9.2. $C_{17}H_{14}N_2S.HCl$ requires C,64.85; H,4.8; N,8.9%).

EXAMPLE 8

Following the general procedure of Example 1 the following products are prepared:

| Starting Material | | Final Product | |
|---|---|---|---|
| IIIb | | IIb | Ib |
| (8a) | IIIb $R^1$ = 8-Me<br>$R^2$ = H | $PhCH_2Cl$ | $R^1$ = 8-Me<br>$R^2$ = H<br>A = $CH_2$<br>Ar = Ph |
| (8b) | IIIb $R^1$ = 8-MeO<br>$R^2$ = H | $PhCH_2Cl$ | $R^1$ = 8-MeO<br>$R^2$ = H<br>A = $CH_2$<br>Ar = Ph |
| (8c) | IIIb $R^1$ = 9-Me<br>$R^2$ = H | $PhCH_2Cl$ | $R^1$ = 9-Me<br>$R^2$ = H<br>A = $CH_2$<br>Ar = Ph |
| (8d) | IIIb $R^1$ = 7-MeO<br>$R^2$ = H | $PhCH_2Cl$ | $R^1$ = 7-MeO<br>$R^2$ = H<br>A = $CH_2$<br>Ar = Ph |
| (8e) | IIIb $R^1$ = 8-Cl<br>$R^2$ = H | $PhCH_2Cl$ | $R^1$ = 8-Cl<br>$R^2$ = H<br>A = $CH_2$<br>Ar = Ph |
| (8f) | IIIb | | |

| Starting Material | | Final Product |
|---|---|---|
| indoline-SH | PhCH₂Cl→ | indoline-SCH₂Ph |
| (8g) IIIb benzazepine-SH | PhCH₂Cl→ | benzazepine-SCH₂Ph |

EXAMPLE 9

The starting material PhCH₂Cl in Examples 8a to 8g is replaced by 4-chlorobenzylchloride to obtain the corresponding final products.

EXAMPLE 10

The starting material PhCH₂Cl in Examples 8a to 8g is replaced by PhCH(CH₃)Cl to obtain the corresponding final products.

EXAMPLE 11

The starting material PhCH₂Cl in Examples 8a to 8g is replaced by 1-naphthylmethylchloride to obtain the corresponding final products.

Pharmacological Test Results

| Compound Example No. | Stress Induced Erosion (Senay & Levine) | | Anti-Secretory (Shay et al) | % Inhibition to Stimulation by | |
|---|---|---|---|---|---|
| | Dose mg/kg | % Inhibition | | DBcAMP at $10^{-4}$ | K⁺ at $10^{-4}$ |
| 1 | 100 | 83 | 30 N/A | 70 | 111 |
| 2 | 100 | N/A | 30 N/A | 69 | 54 |
| 3 | 100 | 62% | 30 N/A | 6.7 | 76 |
| 4 | 100 | 55% | 30 N/A | 32.9 | 83.5 |
| 5 | 100 | N/A | 30 N/A | 53 | 109 |
| 6 | 100 | N/A | 30 N/A | 40.6 | 93 |
| 7 | 100 | 54 | 30 N/A | 40 | 63 |

N/A = No significant Activity.

What is claimed is:

1. A compound of formula I

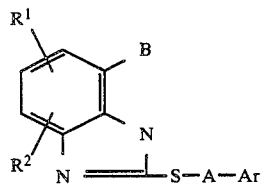

wherein
A is a $C_1$–$C_4$ straight or branched alkylene chain which may be saturated or unsaturated;
B is a $C_2$–$C_4$ straight or branched alkylene chain which may be saturated or unsaturated;
Ar is a phenyl or naphthyl group which may be mono or polysubstituted with halogen, $C_1$–$C_6$-alkoxy, $C_7$–$C_{12}$-aralkoxy, hydroxy, $C_1$–$C_6$-hydroxyalkyl, $C_1$–$C_6$-alkoxyalkyl, trifluoromethyl, $C_1$–$C_6$-alkyl, phenyl, naphthyl or $C_7$–$C_{12}$-aralkyl or disubstituted with a $C_1$–$C_6$-alkylene dioxy radical;
$R^1$ and $R^2$ are the same or different and are hydrogen, $C_1$–$C_6$-alkyl, $C_1$–$C_6$-alkoxy, $C_1$–$C_6$-alkoxyalkyl, $C_1$–$C_6$-hydroxyalkyl, hydroxy, halogen, nitro, carboxy, $C_1$–$C_6$-alkanoylamino, $C_1$–$C_6$-alkoxycarbonyl, carbamoyl, carbamoyloxy, cyano, $C_1$–$C_6$-alkanoyl or trifluoromethyl, or an acid addition salt thereof.

2. A compound as claimed in claim 1, wherein Ar is phenyl or halophenyl.

3. A compound as claimed in claim 1, wherein B is (CH₂)₃ and A is CH₂.

4. A compound as claimed in claim 1, wherein $R^1$ and $R^2$ are hydrogen.

5. A compound selected from 2-benzylthio-5,6,-dihydro-[4H]-imidazo[4,5,1-ij]-quinoline, or an acid addition salt thereof;
2-(4-chlorophenylmethylthio)-5,6-dihydro-[4H]-imidazo-[4,5,1-ij]quinoline, or an acid addition salt thereof; or
5,6-dihydro-2-(2-fluorophenylmethylthio)-[4H]-imidazo-[4,5,1-ij]quinoline, or an acid addition salt thereof.

6. A compound selected from 2-(3-chlorobenzylthio)-5,6,-dihydro-[4H]-imidazo-[4,5,1-ij]quinoline, or an acid addition salt thereof; 5,6-dihydro-2-(4-fluorophenylmethylthio)-[4H]-imidazo-[4,5,1-ij]quinoline, or an acid addition salt thereof;
2-(2-chlorophenylmethylthio)-5,6-dihydro-[4H]-imidazo [4,5,1-ij]quinoline, or an acid addition salt thereof; or 2-benzylthio-[4H]-imidazo[4,5,1-ij]quinoline, or an acid addition salt thereof.

7. A method of treating ulcers or hypersecretion in a mammal in need of such treatment which method comprises treating said mammal with an anti-ulcer or anti-hyper-secretion effective amount of a compound as claimed in claim 1 or an acid addition salt thereof.

8. A pharmaceutical composition for use in the treatment of ulcers or hypersecretion comprising an anti-ulcer or anti-hypersecretion effective amount of a compound of formula I as claimed in claim 1, or a pharmaceutically acceptable acid addition salt thereof, and a pharmaceutical carrier.

9. A pharmaceutical composition as claimed in claim 8, in unit dosage form.